United States Patent [19]

Wollmann et al.

[11] Patent Number: 6,093,844
[45] Date of Patent: Jul. 25, 2000

[54] METHOD OF PRODUCING ALKALINE-EARTH SALTS OF ALIPHATIC β-KETO COMPOUNDS

[75] Inventors: Gerhard Wollmann, Hilden; Joerg-Dieter Klamann, Bremerhaven; Guido Sonnen, Moers, all of Germany

[73] Assignee: Henkel Kommanditgesellschaft auf Aktien (KGaA), Duesseldorf, Germany

[21] Appl. No.: 09/142,783

[22] PCT Filed: Mar. 7, 1997

[86] PCT No.: PCT/EP97/01156

§ 371 Date: Sep. 15, 1998

§ 102(e) Date: Sep. 15, 1998

[87] PCT Pub. No.: WO97/34859

PCT Pub. Date: Sep. 25, 1997

[30] Foreign Application Priority Data

Mar. 15, 1996 [DE] Germany .............. 196 10 320

[51] Int. Cl.⁷ .............. C07C 69/66; C07C 69/72
[52] U.S. Cl. .............. 560/174; 560/178; 560/179; 568/318; 568/350
[58] Field of Search .............. 560/178, 174, 560/179; 568/318, 350

[56] References Cited

U.S. PATENT DOCUMENTS 3,474,464  10/1969  Matthews .............. 260/429
5,194,671   3/1993  Meier .............. 560/126

FOREIGN PATENT DOCUMENTS

| 0 514 893 | 11/1992 | European Pat. Off. |
| 1 576 711 | 8/1969 | France . |
| 1 039 056 | 9/1958 | Germany . |
| 51-54691 | 5/1976 | Japan . |
| 52-136 131 | 11/1977 | Japan . |
| WO91/13051 | 9/1991 | WIPO . |

OTHER PUBLICATIONS

Z.H. Obsche Khim 42, pp. 402–403 (1972).

J. Chem. Soc., (1951): pp. 2505–2506.

Compt. Rend., 157, pp. 50–52 (1913).

*Primary Examiner*—Gary Geist
*Assistant Examiner*—Robert W. Deemie
*Attorney, Agent, or Firm*—Ernest G. Szoke; Wayne C. Jaeschke; Glenn E.J. Murphy

[57] ABSTRACT

Proposed is a method of producing alkaline-earth salts of aliphatic β-keto compounds by reacting alkaline-earth hydroxides with aliphatic β-ketoesters and/or β-diketones in the absence of solvent to give the corresponding alkaline-earth salts. The β-keto compound is added in portions to the powdered alkaline-earth hydroxide and the reaction mixture subsequently dried. Good yields are obtained of a fine-grained, light colored product.

6 Claims, No Drawings

METHOD OF PRODUCING ALKALINE-EARTH SALTS OF ALIPHATIC β-KETO COMPOUNDS

FIELD OF THE INVENTION

This invention relates to a process for the production of alkaline earth metal salts of aliphatic β-keto compounds by reaction of aliphatic β-keto esters or β-diketones with an alkaline earth metal hydroxide in the absence of a solvent to form the corresponding alkaline earth metal salts, the reaction being carried by introducing the powder-form alkaline earth metal hydroxide first and adding the β-keto compound in portions.

DISCUSSION OF RELATED ART

Alkaline earth metal salts of aliphatic β-keto compounds, such as for example calcium salts of ethyl acetoacetate and acetyl acetone, are normally used as nontoxic stabilizers for PVC instead of the toxic lead compounds. A process for the production of a calcium salt of ethyl acetoacetate by treatment of ethyl acetoacetate with metallic calcium in absolute ethanol is known from Z. h. Obsche Khim 42 403 (1972). The use of metallic calcium makes this process very complicated and expensive. Another process in which ethyl acetoacetate is treated with calcium carbonate or calcium oxide in absolute benzene is described in J. Chem. Soc., 1951, 2505. The reaction with calcium oxide is characterized by a very low reaction rate whereas the use of calcium carbonate involves relatively high costs and dosing problems. In both cases, extremely high viscosities occur during the reaction and the color of the products is too dark. DE 1 039 056 describes a process for the synthesis of alkaline earth metal salts of acetyl acetone in which acetyl acetone is treated with ammonia and the ketimine formed is reacted with a metal salt. Although, in this case, a relatively high reaction rate is achieved through the use of calcium hydroxide, high viscosities again occur during the reaction and the products are again dark in color. In addition, all the processes mentioned above use organic solvents although the use of such solvents should largely be avoided on ecological grounds. According to Compt. Rend., 157, 50 (1913), acetyl acetone may also be reacted with a metal hydroxide in aqueous solution. JP 51-54691 describes another process for the production of alkaline earth metal salts of aliphatic keto compounds in which the alkaline earth metal hydroxide is added in portions to the aliphatic β-keto ester and/or β-diketones in the absence of a solvent. The two processes do not use organic solvents. However, it has been found in these processes that a phase of extremely high viscosity occurs during the reaction, causing the mixer to come to a standstill. The process is therefore very difficult to handle, in addition to which caking of the product mixture can occur on the walls of the reactor. In addition, the product obtained is still relatively dark in color and consists of coarse particles.

Accordingly, the problem addressed by the present invention was to provide a solventless process which would give light-colored fine-particle products and in which the occurrence of an extremely high-viscosity phase could be avoided so that the reaction would be easier to control.

DESCRIPTION OF THE INVENTION

Accordingly, the present invention relates to a process for the production of alkaline earth metal salts of aliphatic β-keto compounds by reaction of alkaline earth metal hydroxides with aliphatic β-keto esters and/or β-diketones in the absence of a solvent to form the corresponding alkaline earth metal salts, in which a) the powder-form alkaline earth metal hydroxide is introduced first into the reactor and the aliphatic β-keto compound is added in portions and b) the reaction mixture is subjected to a drying step.

It has now surprisingly been found that the occurrence of a high-viscosity phase can be avoided by adding the β-keto compound in portions to the powder-form alkaline earth metal salt introduced first into the reactor. This makes the reaction easier to control and eliminates the caking of product on the walls of the reactor. In addition, the products obtained in yields of more than 90% are distinguished by a light color and consist of very fine particles.

Aliphatic β-keto esters and aliphatic β-diketones

The aliphatic β-keto esters and aliphatic β-diketones to be used in accordance with the invention are represented by the following formula:

$$R^1COCH_2COR^2 \qquad (I),$$

in which $R^1$ is an alkyl group and $R^2$ is an alkyl or alkoxy group. According to the invention, particularly preferred compounds (I) are those in which $R^1$ and $R^2$ each represent a short-chain alkyl or alkoxy group containing 1 to 3 carbon atoms. Ethyl acetoacetate, methyl acetoacetate and acetyl acetone are particularly preferred.

Alkaline earth metal hydroxides

According to the invention, any alkaline earth metal hydroxides may be used, those selected from the group consisting of calcium hydroxide, magnesium hydroxide and barium hydroxide being preferred. The aliphatic β-keto compound and the alkaline earth metal hydroxide are preferably used in stoichiometric ratios (2:1).

Procedure

The alkaline earth metal hydroxide is introduced in powder form into a kneader, dryer or mixer, the liquid β-keto compound is added at room temperature and the two educts are thoroughly mixed. The addition is made in such a way that the reaction product retains its powder form so that its viscosity stays the same. Because the reaction is exothermic, the reaction temperature gradually increases but never exceeds 40° C. After all the β-keto compound has been added and the main reaction completed, the drying step is carried out. The water of reaction can be removed by applying a vacuum of 10 to 50 mbar and preferably 20 to 40 mbar and/or reducing the vapor pressure by a gas stream, preferably of an inert gas, and/or increasing the temperature to values of 60 to 150° C. and preferably 70 to 120° C. Yields of more than 90% are obtained. After the drying step, the alkaline earth metal salt accumulates in the form of a fine-particle powder.

In one particularly preferred embodiment, the reaction is carried out at room temperature in a List dryer with thorough mixing of the reactants. After the β-keto compound has been added to the powder-form alkaline earth metal hydroxide and the main reaction has been completed, a large part of the water of reaction is first driven out with an inert gas, preferably nitrogen, after which the reactor is heated to a temperature of 90 to 120° C. and the remaining water is removed under a pressure of 30 to 40 mbar without the acetyl acetone escaping. The reaction equilibrium is thus shifted and the yield increased.

EXAMPLES

Example 1

740 g of calcium hydroxide (9.98 moles) were introduced into a 5-liter List dryer and 2,000 g of acetyl acetone (19.98 moles) were added over a period of 40 minutes during which the reactants were thoroughly mixed. Most of the water of reaction was removed towards the end of the reaction by stripping with nitrogen. Vacuum was then applied to the system. Under a pressure of 30 mbar, the dryer was heated to 70° C. to eliminate the residual moisture. A fine light powder was obtained as the product. The conversion of calcium hydroxide amounted to 94%.

Comparison Example 1

2,000 g of acetyl acetone (19.98 moles) were introduced into a List dryer and 740 g of calcium hydroxide (9.98 moles) were then added with thorough mixing of the reactants. During the addition of the calcium hydroxide, large lumps were formed and caking of reaction product occurred on the walls of the reactor and the blades. The water of reaction was removed by stripping with nitrogen and applying a vacuum of 30 mbar and, at the same time, increasing the temperature to 70° C. The product obtained was a coarse powder with distinct lumps and a dark yellowish color. The conversion of calcium hydroxide amounted to 52%.

We claim:

1. A process for the production of an alkaline earth metal salt of an aliphatic β-keto compound, comprising:

a) reacting, in the absence of a solvent, a quantity of an alkaline earth metal hydroxide with a quantity of a β-keto compound selected from the group consisting of aliphatic β-keto esters and aliphatic β-diketones, wherein the quantity of alkaline earth metal hydroxide, in powder form, is introduced into a reactor and the quantity of aliphatic β-keto compound is added to the reactor in portions to form a reaction mixture, said portions of the quantity of β-keto compound being added such that the reaction mixture retains a powder form; and b) subjecting the reaction mixture to a drying step.

2. A process according to claim 1, wherein the aliphatic β-keto compound is selected from the group consisting of ethyl acetoacetate, methyl acetoacetate, acetyl acetone, and mixtures thereof.

3. A process according to claim 1, wherein the alkaline earth metal hydroxide is selected from the group consisting of calcium hydroxide, magnesium hydroxide, barium hydroxide, and mixtures thereof.

4. A process according to claim 1, wherein the β-keto compound is added to the reactor at room temperature.

5. A process according to claim 1, wherein the drying step is effected by a means selected from the group consisting of reduced pressure, increased temperature, stripping with an inert gas, and combinations thereof.

6. A process for the production of an alkaline earth metal salt of an aliphatic β-keto compound, comprising:

a) reacting, in the absence of a solvent, a quantity of an alkaline earth metal hydroxide selected from the group consisting of calcium hydroxide, magnesium hydroxide, barium hydroxide, and mixtures thereof with a quantity of an aliphatic β-keto compound selected from the group consisting of ethyl acetoacetate, methyl acetoacetate, acetyl acetone, and mixtures thereof, wherein the quantity of alkaline earth metal hydroxide, in powder form, is introduced into a reactor and the quantity of aliphatic β-keto compound is added to the reactor in portions at room temperature to form a reaction mixture, said portions of the quantity of β-keto compound being added such that the reaction mixture retains a powder form; and b) subjecting the reaction mixture to a drying step effected by a means selected from the group consisting of reduced pressure, increased temperature, stripping with an inert gas, and combinations thereof.

* * * * *